(12) United States Patent
Lynch et al.

(10) Patent No.: US 7,658,948 B2
(45) Date of Patent: Feb. 9, 2010

(54) FOAMING GRANULE AND METHOD FOR MAKING SAME

(75) Inventors: James R. Lynch, Toledo, OH (US); Timothy D. Birthisel, Perrysburg, OH (US); Jeffrey J. Fesko, Maumee, OH (US)

(73) Assignee: The Andersons, Inc., Maumee, OH (US)

( * ) Notice: Subject to any disclaimer, the term of this patent is extended or adjusted under 35 U.S.C. 154(b) by 83 days.

(21) Appl. No.: 11/327,098

(22) Filed: Jan. 6, 2006

(65) Prior Publication Data

US 2006/0178271 A1   Aug. 10, 2006

Related U.S. Application Data

(60) Provisional application No. 60/642,318, filed on Jan. 7, 2005.

(51) Int. Cl.
*A61K 9/14* (2006.01)
*A61K 9/16* (2006.01)

(52) U.S. Cl. ...................... 424/489; 424/490

(58) Field of Classification Search .............. 424/458, 424/489, 490
See application file for complete search history.

(56) References Cited

U.S. PATENT DOCUMENTS

| | | | |
|---|---|---|---|
| 5,948,439 A | 9/1999 | Forman et al. | |
| 6,200,928 B1 * | 3/2001 | Kawai | 504/117 |
| 6,506,713 B1 | 1/2003 | Slavtcheff et al. | |
| 6,800,597 B2 | 10/2004 | Campagnoli | |

FOREIGN PATENT DOCUMENTS

JP          07112904        *   5/1995

\* cited by examiner

*Primary Examiner*—Alton N Pryor
(74) *Attorney, Agent, or Firm*—Gifford, Krass, Sprinkle, Anderson & Cikowski, P.C.

(57) ABSTRACT

A foaming granule is provided that includes an acid, a gas-evolving acid neutralizing agent, a surfactant foaming agent, and an active agent that is a plant growth enhancer, pest control agent, de-icer or anti-icer. Upon wetting a granule, the acid and neutralizing agent are brought into contact releasing gas that is trapped in the surfactant to form a foam that disperses the active agent to a greater area and more uniformly than a conventional nonfoaming granule containing a like amount of active agent. Dispersal of granules followed by sufficient time for foaming to occur represents a typical use methodology.

17 Claims, No Drawings

FOAMING GRANULE AND METHOD FOR MAKING SAME

RELATED APPLICATION

This application claims priority of U.S. Provisional Patent Application Ser. No. 60/642,318 filed Jan. 7, 2005, which is incorporated herein by reference.

FIELD OF THE INVENTION

The present invention in general relates to a dispersible granule for use in plant culture or for de-icing and anti-icing of paved surfaces and equipment, and, in particular, to a granule that foams upon contact with water.

BACKGROUND OF THE INVENTION

In the course of a growing season, modern plant culture dictates multiple treatments with fertilizer and pesticide, and in winter, where snow and ice are present for periods of time, proper property and equipment (e.g. aviation) maintenance requires the application of de-icing and anti-icing materials. A practitioner of plant culture must decide whether a particular treatment is best performed with a granular product or a liquid spray application. Crops as diverse as turf, grain crops, tubers, ground fruits and vegetables, and horticultural plantings are routinely treated with either granular or sprayed substances. Facility and equipment maintenance operations likewise employ either granular de-icers or liquid compositions, so a similar choice must be made by that practitioner. Each application method has limitations. Specifically, while granule broadcast tends to provide a simple broadcast, generally long-term release and safe handling, granules are difficult to adhere to plant and equipment surfaces, create concentration gradients about each granule, and represent an ongoing potential toxin or physical entity that can be inadvertently contacted or ingested by humans or fauna, or pose mechanical problems for equipment such as maintenance and aviation equipment. In contrast, spray treatment generally requires considerable skill for application, contacts only exposed foliage and equipment and surfaces receiving indirect drainage from other surfaces, and tends to dissipate, or "run off," quickly. Some sprays such as anti-icers require the use of expensive polymers and additives in order to prolong the "holdover time," or length of time the equipment may be allowed to stand ice free before it is put into service. Based on these treatment characteristics, pesticides targeting weed leaves or foliage-feeding pests and de-icers and anti-icers targeting equipment surfaces tend to be applied as a liquid spray, while fertilizers and pesticides targeting weed seeds, grubs and other soil-dwelling pests and de-icers and anti-icers targeting paved surfaces often are delivered as granules. Regardless of whether spray or granule broadcast is used, the application method is not completely satisfactory. For instance, spray application fails to reach pests dwelling on the underside of foliage and is quickly dissipated and leached into soil by rain, and liquid de-icers and anti-icers can cause environmental wastewater management problems because a significant excess amount of product must be used in order to allow for adequate contact time.

Granular pesticide formulations often require the use of additional pesticide due to inefficiencies in the timely release, or efficient environmental extraction, of the pesticide from the associated granular substrate materials.

Thus, there exists a need for a granule that, through foaming upon contact with water, has desirable attributes of both granule, broadcast and spray treatment for use in plant culture and/or in de-icing and anti-icing.

Additionally, the use of a foaming mechanism offers another tool for pest control, which may augment or replace the traditional pesticide material in certain cases. By generating a gas, along with a temporary containment for the gas, which may be directly toxic to, or which may alter the behavior of certain animal pests, the invention may serve as a pesticide or synergist in its own right.

The foaming mechanism as applied to de-icers can significantly enhance product distribution, adhesion, penetration of ice/snow cover, and separation of ice/snow from the treated surfaces due to the chemical and kinetic energy it provides. Likewise, the mechanism may enhance the use of exothermic energy (from dissolution of certain salts, e.g. calcium chloride).

SUMMARY OF THE INVENTION

A foaming granule is provided that includes an acid, a gas-evolving acid neutralizing agent, a surfactant foaming agent, and an active agent that is a plant growth enhancer, pest control agent, de-icer or anti-icer. Upon wetting a granule, the acid and neutralizing agent are brought into contact releasing gas that is trapped in the surfactant to form a foam that disperses the active agent to a greater area and more uniformly than a conventional nonfoaming granule containing a like amount of active agent. Dispersal of granules followed by sufficient time for foaming to occur represents a typical use methodology.

DETAILED DESCRIPTION OF THE PREFERRED EMBODIMENTS

The present invention has utility as a granule to deliver a substance beneficial to plant culture. An inventive granule, upon contact with water, releases gas to create a foam that spreads the granule contents beyond the dimensions of the granule. The use of an inventive granule achieves superior handling and active ingredient usage as compared to the conventional art.

The present invention incorporates a solid acid-neutralizing agent and an acid that are not completely reactive until solvated with water. Neutralization of the acid component by a carbonate, peroxide, or azide liberates a gas that functions as a propellant to expand a foaming agent present within a composition according to the present invention. A gas-evolving neutralizing agent according to the present invention generates a gas such as carbon dioxide, nitrogen or oxygen upon reaction with the acid in the presence of water. A carbonate, peroxide, or azide operative in the present invention as a neutralizing agent is one capable of neutralizing acid. Carbonates operative herein include carbonates where the cation is an alkali metal, alkali earth, hydrogen, ammonium, tetraorganal ammonium, transition metals, alone, or in combination with hydrogen. Peroxides operative herein illustratively include sodium perborate and sodium percarbonate. Sodium azide is an exemplary azide operative herein. It is appreciated that in selecting a carbonate, peroxide, or azide, the tolerance of a target plant and the healthy soil ecosystem surrounding the plant towards the carbonate chitin are important considerations. Specific examples of carbonates operative herein illustratively include sodium carbonate, sodium bicarbonate, magnesium carbonate, calcium carbonate, aluminum carbonate, and ammonium carbonate. It is appreciated that inventive carbonate is typically in the form of a mineral particulate. Additionally, it is appreciated that the ability of a carbonate to neutralize acid, and in the process deliver a carbon dioxide, is largely independent of the nature of the cation and as such, the choice of a particular carbonate is dictated by factors illustratively including cost, ease of processing, and secondary soil conditioning properties. By way of example, a soil deficient in a particular element such as calcium or magnesium derives a secondary soil conditioning benefit from the use of these respective carbonates. Likewise, ammonium carbonate, after acid neutralization, provides a bioavailable nitrogen source. The gas-evolving neutralizing agent is present from 1 to 80 wt. %; preferably the gas-evolving neutralizing agent is present in a stoichiometric amount relative to the acid equivalents of the acid component.

The only requirements as to the identity of an acid operative in the present invention are that the acid have a pKa value sufficient to generate a high enough proton ion concentration to induce active carbon dioxide generation and that the acid salt be compatible with plant culture. Preferably, the acid is in a solid and dry form. An important component of an inventive granule is the acidic material. Suitable for this purpose are any acids present in dry solid form. Acids operative herein include $C_2$-$C_{20}$ organic mono- and poly-carboxylic acids and especially alpha- and beta-hydroxycarboxylic acids; $C_2$-$C_{20}$ organophosphorus acids such as phytic acid; and $C_2$-$C_{20}$ organosulfur acids such as toluene sulfonic acid. Typical hydroxycarboxylic acids include gluconic, glucoheptonic, 2-hydroxyisovaleric, tartaric, lactic, salicylic and citric acids as well as acid forming lactones such as gluconolactone and glucarolactone. Still other specific acids operative herein illustratively include formic, acetic, propionic, butyric, valeric, caproic, caprylic, capric, lauric, myristic, palmitic, stearic, oleic, linoleic, linolenic, propionic, benzoic, toluic, anthranilic, and acrylic, as well as dicarboxylic acids such as oxalic, adipic, glutaric, succinic, malonic, succinic, glutaric, adipic, maleic, fumaric, malic, maleic, and phthalic acids. Most preferred is citric acid. Also suitable as acid material may be encapsulated acids. Typical encapsulating material may include water soluble synthetic or natural polymers such as polyacrylates (e.g. encapsulating polyacrylic acid), cellulosic gums, polyurethane and polyoxyalkylene polymers.

Optionally, an acid salt of the acid used is present as a pH buffer and to provide storage stability to the resulting composition.

A surfactant foaming agent is present to entrain carbon dioxide emitted upon neutralization reaction between the acid and the gas-evolving neutralizing agent. A surfactant foaming agent is typically present from 0.01 to 10 per weight percent. Surfactant foaming agents operative herein illustratively include sopinin; anionic surfactants, such as fatty acid esters, alkyl sulfates, alkylarylsulfonates, such as alkylbenzene sulfonates; alkyl sulfonates; isocyanates, such as methylenedisocyanate and tolylene diisocyanate, and nonionic surfactants, such as polyoxyethylene alkyl phenols, polyoxyethylene fatty acids esters, polyoxyethylene alcohols, polyoxyethylene mercaptans, polyoxyethylene alkylamines, polyol esters, phosphate esters, alkyl mono- or poly glycosides, sorbitan esters, polymers of ethylene oxide, propylene oxide, and/or butylene oxide, vegetable oil glycerides, glycerol esters, silicones, and various compounds containing amide groups.

An inventive granule includes an active ingredient such as a plant growth enhancer, a de-icer, an anti-icer, a pest control agent fertilizer, and a combination thereof. An active ingredient is typically present in an amount ranging from 0.05% to 50% by weight of the total dry weight of the particle. In a more preferred embodiment, the active ingredient is present in an amount ranging from 0.1% to 30% by weight of the total dry weight of the granule. In a still more preferred embodiment, the active ingredient is present in an amount ranging from 0.5% to 10% by weight of the total dry weight of the particle. Optionally, a foam stabilizing agent is included in order to maintain the presence of the foam over time. Compounds such as glycerin, hydrolyzed protein, synthetic polymers, or any of a number of long chain polar compounds with straight chain hydrocarbon groups of about the same length as the surfactant, may serve this purpose.

As used herein, a plant growth enhancer is defined as a substance that enhances the growing medium in which a plant resides. A plant growth enhancer specifically includes a bioavailable source of nitrogen, potassium, or phosphorus; a soil nutrient; a soil amendment material; and a biostimulant. Exemplary fertilizers and de-icers include urea, sulfur-coated urea, isobutylidene diurea, ammonium nitrate, ammonium sulfate, ammonium phosphate, triple super phosphate, phosphoric acid, potassium sulfate, potassium nitrate, potassium metaphosphate, potassium, dipotassium carbonate, potassium oxide and a combination thereof.

Exemplary soil nutrients include calcium, magnesium, sulfur, iron, manganese, copper, zinc; oxides thereof; salts thereof, and a combination thereof.

Exemplary amendment materials include humic acid, blood meal, bone meal, seed meal, feather meal, soy meal, meat meal, animal waste, activated sludge, hydrolyzed animal hair, a fish byproduct, chitin, composts and a combination thereof. In addition, a fertilizer particle optionally includes an additive to aid in particle formation illustratively including an anti-dust agent, an anti-caking agent, a filler, a preservative, and a combination thereof.

Biostimulants are substances that promote plant survival and health and illustratively include plant growth hormones and plant growth regulators such as cytokinins, auxins, gibberellins, ethylene, absisic acid and a combination of these. A biostimulant is optionally included as a secondary active ingredient in an amount ranging from 0.05% to 10% by weight of the total dry weight of the particle. In a more preferred embodiment, the biological factor or biostimulant active ingredient is present in an amount ranging from 0.1% to 5% by weight of the total dry weight of the particle. In a still more preferred embodiment, the biological factor or biostimulant active ingredient is present in an amount ranging from 0.25% to 1% by weight of the total dry weight of the particle.

Exemplary de-icers include glycols, salts of carboxylic acids, sodium-, magnesium-, and calcium-chlorides. Exemplary anti-icers illustratively include thickened aqueous alcohols as detailed in U.S. Pat. No. 5,772,912; or a deicer that affects the colligative properties of water to depress the freezing temperature below $-10°$ C.

In another embodiment, an inventive granule includes as an active substance a pest control agent for killing or inhibiting infestation by a target pest organism includes an arachnid; a bacterium; a bird; a fungus; an insect; a mammal, such as a rodent; a mollusk, such as a snail or a slug; a virus; and a worm. The pest control agent is appreciated to be operative not only in being lethal to the pest but also by being repellant or lessen the reproductive fitness of the pest.

A pesticide control agent includes agents such as an acaracide, an antimicrobial, a bactericide, an entomopathogen, a fungicide, a synthetic plant growth regulator such as a gibberlic acid synthesis inhibitor or promoter, an herbicide, an insecticide, a molluskicide, a nemacide, a rodenticide, a pheromone, a chemosterilant, a viricide, an imagocide, a larvicide, an ovicide, a formicide, an aphidicide, a muscacide, a culicicide, an anophelicide, an arachnidcide, and a vespacide. Preferably, an inventive bait particle containing a toxic invertebrate pesticide also contains a mammalian and/or avian ingestion repellant. More preferably, it also contains both mammalian and avian ingestion repellants to lessen the likelihood of incidental ingestion by bystander higher species. Mammalian ingestion repellants illustratively include cadaverine, butyric acid, and capsaicin. Avian repellants include artificial grape flavorant.

A pest reproductive control agent operative herein includes a pheromone, molting signaling compound or steroid that upon contact with the target pest decreases the reproductive capacity of the pest. A pest reproductive control agent is preferred over a pesticide since a reproductive control agent is specific to a species or narrower group of organisms, does not bioaccumulate, and is less detrimental to predatory or bystander organisms in the pest habitat. Additionally, a reproductive control agent is unlikely to avoid the bait due to ill health effects associated with sampling, as is often the case with a lethal pesticide.

In addition to the acid, gas-liberating neutralizing agent, surfactant foaming agent, and active ingredient, an inventive granule optionally contains a filler and/or binder. A filler operative herein is intended to provide a low-cost volume enhancement. Fillers operative herein illustratively include cereal or grain hulls, peanut hulls, plant pulp, other plant-based cellulose materials, and clays. A filler is typically present from 0.1 to 99.9 total weight percent and preferably from 5 to 98 total weight percent.

Optionally, an inventive granule has a binder component present in an amount ranging from 5% to 75% by weight of the total dry weight of the granule. In a further embodiment, the binder component is present in an amount ranging from 1% to 25% by weight of the total dry weight of the granule. A binder component is included in a granule as necessary to produce or promote cohesion in forming a particle capable of retaining a specified form during transport and/or distribution. A binder component may be bentonite clay, carbohydrate, protein, lipid, synthetic polymer, glycolipid, glycoprotein, lipoprotein, lignin, a lignin derivative, a carbohydrate-based composition, and a combination thereof. In a preferred embodiment the binder component is a lignin derivative and is optionally calcium lignosulfonate. Alternatively, the binder component is selected from the group consisting of: a monosaccharide, a disaccharide, an oligosaccharide, a polysaccharide and combinations thereof. Specific carbohydrate binders illustratively include glucose, mannose, fructose, galactose, sucrose, lactose, maltose, xylose, arabinose, trehalose and mixtures thereof such as corn syrup; celluloses such as carboxymethylcellulose, ethylcellulose, hydroxyethylcellulose, hydroxy-methylethylcellulose, hydroxyethylpropylcellulose, methylhydroxyethyl-cellulose, methylcellulose; starches such as amylose, seagel, starch acetates, starch hydroxyethyl ethers, ionic starches, long-chain alkyl starches, dextrins, amine starches, phosphates starches, and dialdehyde starches; plant starches such as corn starch and potato starch; other carbohydrates such as pectin, amylopectin, xylan, glycogen, agar, alginic acid, phycocolloids, chitin, gum arabic, guar gum, gum karaya, gum tragacanth and locust bean gum; vegetable oils such as corn, soybean, peanut, canola, olive and cotton seed; complex organic substances such as lignin and nitrolignin; derivatives of lignin such as lignosulfonate salts illustratively including calcium lignosulfonate and sodium lignosulfonate and complex carbohydrate-based compositions containing organic and inorganic ingredients such as molasses. Suitable protein binders illustratively include soy extract, zein, protamine, collagen, and casein. Binders operative herein also include synthetic organic polymers capable of promoting or producing cohesion of particle components and such binders illustratively include ethylene oxide polymers, polyacrylamides, polyacrylates, polyvinyl pyrrolidone, polyethylene glycol, polyvinyl alcohol, polyvinylmethyl ether, polyvinyl acrylates, polylactic acid, and latex. In a preferred embodiment, the binder is calcium lignosulfonate, molasses, a liquid corn starch, a liquid corn syrup or a combination thereof.

An inventive granule is produced by a number of processes. In the preferred process, the granule components, with the exclusion of either the acid or gas-emitting neutralizing agent, are wet granulated through a process of steps, including mixing of various dry components, wet massing the dry powder mixture with liquid surfactants, binders or the like, alone or with the addition of a solvent to arrive at a suitable consistency for granulating. Upon forming a granule, the excluded acid or gas-evolving neutralizing agent is either powder coated onto the surface of the granule, alone, or with a binder as detailed herein, to adhere a predetermined and preferably stoichiometrically-balanced amount of the omitted acid or neutralizing agent to complete acid neutralization. Of the binders detailed herein, methylene urea is particularly preferred. Alternatively, a granule is coated with a polymeric acid, such as a polyacrylate, thereby affording a free-flowing granule with a passivating surface coat. Alternatively, a granule omitting either an acid or neutralizing agent is impregnated with the omitted ingredient through solvent impregnation. The solvent means are selected to carry the omitted ingredient into the interior of the granule without complete activation of the acid neutralization reaction. As such, aqueous solvent is an unacceptable solvent, whereas anhydrous alcohols, ethers, tetrahydrofuran, and alkanes are generally suitable. It is appreciated that solvent impregnation is enhanced by allowing some gas formation, so as to open pores within the granule, thereby enhancing impregnation. Alternatively, welling of a granule, a solvent carrying the omitted ingredient, followed by increasing the temperature, so as to volatize the solvent, is also operative herein.

An alternative embodiment from the inventive granule involves compressing a powder mixture into a large form that is subsequently ground to a desired size. It is appreciated that dry granulation is facilitated by the addition of a pressing agent, such as a stearate salt.

In instances where the acid component exists as a hydrated powder, a fusion method is available in which to form an inventive granule. Heating of the mixed powder dissociates water from the acid, thereby causing some gas evolution, resulting in a pliable mass that is amenable to pass through a sizing screen. As heating temperatures typically are required in the range of 80-150° C., it is appreciated that the inclusion of the active ingredient subsequent to granule formation and drying is preferred. Subsequent addition of an active ingredient occurs through coating of the granule so formed with a binder solution containing the active ingredient. The resulting granule includes the desired amount of the active ingredient and has a sealant coat that impedes atmospheric degradation of the inventive granule.

In a de-icing or anti-icing use environment, inventive granules are dispersed onto a surface such as a road surface or piece of equipment to react, creating a foam that melts ice or prevents ice formation. It is appreciated that a resultant surfactant film inhibits ice nucleation.

It is appreciated that an inventive granule is operative alone, or as an additive with conventional pelletized substances, such as fertilizer, de-icer, or pest attractant bait.

The present invention is further detailed with respect to the non-limiting examples.

Example 1

13.7 lbs of citric acid is combined with slightly more than 3 mole equivalents of potassium bicarbonate (21.4 lbs as dry powders) in a stainless steel vessel, together with 500 grams of sodium dodecyl sulfate and 10 kilograms of −40 mesh corncob grind. The resulting mixture is heated to 100° C. with constant turning. Upon softening to a paste consistency, the material is urged through a No. 6 sieve and cooled. The resulting granules are then coated with an alcoholic solution of methylene urea containing 0.3% by weight methylparathyon and allowed to dry to a hard-dry coating.

The resulting granules are broadcast onto a wet turf crop field. The granules are observed to adhere to leaf and plant surfaces with acid neutralization-based foaming observed immediately thereafter.

Example 2

21.4 kilograms of potassium bicarbonate is mixed with corncob grind, and sodium dodecyl sulfate in the amounts provided in Example 1, together with 100 grams of methylparathyon. 5 liters of water is added and the resulting slurry is screen granulated through a U.S. No. 4 mesh screen and dried. The resulting granule is coated with a concentrated aqueous solution of polyacrylic acid and flash dried to yield an inventive granule.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A foaming granule comprising:
    an acid;
    a gas-evolving acid neutralizing agent selected from the group consisting of: an inorganic carbonate, inorganic bicarbonate, alkaline peroxide, and alkaline azide, wherein either said acid or said gas-evolving acid neutralizing agent is present as a coating around an interior of the granule;
    a surfactant foaming agent; and
    an active agent selected from the group consisting of: a pest control agent, a de-icer, and an anti-icer, wherein said acid or said gas-evolving acid neutralizing agent absent from said coating is within the interior of the granule.

2. The granule of claim 1, wherein said acid is citric acid.

3. The granule of claim 1, wherein said acid is tartaric acid.

4. The granule of claim 1, wherein said neutralizing agent is said carbonate.

5. The granule of claim 1, wherein said neutralizing agent is said bicarbonate.

6. The granule of claim 1, wherein said surfactant foaming agent is an anionic surfactant.

7. The granule of claim 1, wherein said pest control agent is an insecticide.

8. The granule of claim 1, wherein said coating further comprises a binder.

9. The granule of claim 8, wherein said binder is selected from the group consisting of lignin lignosulfonate salts, nitrolignin and complex carbohydrate-based lignin.

10. The granule of claim 9, wherein said pest control agent is located within said coating.

11. The granule of claim 1 further comprising a foam stabilizing agent.

12. A process for melting or preventing the formation of ice on a surface comprising:
    dispersing a plurality of foaming granules of claim 1 onto the surface having ice thereon or likely to develop ice thereon wherein said active agent is said de-icer or said anti-icer; and
    allowing sufficient time for said plurality of foaming granules to react and release said active agent.

13. A foaming granule comprising:
    an acid;
    a gas-evolving acid neutralizing agent selected from the group consisting of: an inorganic carbonate, inorganic bicarbonate, alkaline peroxide, and alkaline azide, wherein either said acid or said gas-evolving acid neutralizing agent is present as a coating around an interior of the granule;
    a surfactant foaming agent; and
    a plant growth enhancer, wherein said acid or said gas-evolving acid neutralizing agent absent from said coating is within the interior of the granule.

14. The granule of claim 13, wherein said neutralizing agent is said carbonate.

15. The granule of claim 13, wherein said neutralizing agent is said bicarbonate.

16. The granule of claim 13, wherein said surfactant foaming agent is anionic surfactant.

17. The granule of claim 13 further comprising a foam stabilizing agent.

* * * * *